US008728791B2

(12) United States Patent (10) Patent No.: US 8,728,791 B2
Yukawa et al. (45) Date of Patent: May 20, 2014

(54) MICROORGANISM HAVING THE IMPROVED GENE FOR HYDROGEN GENERATION CAPABILITY, AND PROCESS FOR PRODUCING HYDROGEN USING THE SAME

(75) Inventors: Hideaki Yukawa, Kyoto (JP); Masayuki Inui, Kyoto (JP); Akihito Yoshida, Nara (JP); Naoto Torata, Kashihara (JP)

(73) Assignees: Research Institute of Innovative Technology for the Earth, Kyoto (JP); Sharp Corporation, Osaka (JP)

( * ) Notice: Subject to any disclaimer, the term of this patent is extended or adjusted under 35 U.S.C. 154(b) by 1421 days.

(21) Appl. No.: 11/791,731

(22) PCT Filed: Dec. 7, 2005

(86) PCT No.: PCT/JP2005/022463
§ 371 (c)(1),
(2), (4) Date: May 29, 2007

(87) PCT Pub. No.: WO2006/062130
PCT Pub. Date: Jun. 15, 2006

(65) Prior Publication Data
US 2009/0170176 A1 Jul. 2, 2009

(30) Foreign Application Priority Data

Dec. 8, 2004 (JP) .................................. 2004-356084

(51) Int. Cl.
*C12N 9/88* (2006.01)
*C12N 1/20* (2006.01)
*C12N 15/00* (2006.01)
*C12Q 1/00* (2006.01)
*C12Q 1/68* (2006.01)
*C12P 3/00* (2006.01)
*C07H 21/04* (2006.01)

(52) U.S. Cl.
USPC ........... 435/232; 435/4; 435/6.1; 435/252.33; 435/440; 435/320.1; 435/168; 536/23.2

(58) Field of Classification Search
None
See application file for complete search history.

(56) References Cited

U.S. PATENT DOCUMENTS 7,432,091 B2 10/2008 Yukawa et al.

FOREIGN PATENT DOCUMENTS

WO WO 2004/074495 A1 9/2004

OTHER PUBLICATIONS

International Preliminary Report on Patentability mailed Nov. 22, 2007 in corresponding PCT Application No. PCT/JP2005/022463.
International Search Report for PCT/JP2005/022463 mailed Jan. 31, 2006.
"Biotechnological Hydrogen Generation: An Approach to Enhanced Hydrogen-Generation Capability through High-Density Microbial Cell Reaction and Genetic Modification of Cells", Proceedings of the Annual Meeting of the Year of 2003 at Tokyo Japan Society for Bioscience, Biotechnology, and Agrochemistry.
Unden et al., "Oxygen regulated gene expression in facultatively anaerobic bacteria", Antonie Van Leeuwenhoek, vol. 66, No. 1-3, pp. 3-22 (1994).
Sauter et al.,"Mutational analysis of the operon (hyc) determining hydrogenase 3 formation in *Escherichia coli*", Mol. Microbiol., vol. 6, No. 11, pp. 1523-1532 (1992).
Skibinsky et al., Regulation of Hydrogenase-4 Operon of *Escherichia coli* by the $\sigma^{54}$-Dependent Transcriptional Activators FhlA and HyfR, Jour. of Bacteriology, vol. 184, No. 23, pp. 6642-6653 (2002).
Schlensog et al., "Identification and sequence analysis of the gene encoding the transcriptional activator of the formate hydrogenlyase system of *Escherichia coli*," Molecular Microbiology, vol. 4, No. 8, pp. 1319-1327 (1990).
Penfold et al., "Increased hydrogen production by *Escherichia coli* strain HD701 in comparison with the wild-type parent strain MC4100," Enzyme and Microbial Technology, vol. 33, pp. 185-189 (2003).
Yoshida et al "Enhanced Hydrogen Production from Formic Acid by Formate Hydrogen Lyase-Overexpressing *Escherichia coli* Strains" Applied and Environmental Microbiology, vol. 71, No. 11, Nov. 2005, p. 6762-6768.
Yoshida et al "ERRATUM, Enhanced Hydrogen Production from Formic Acid by formate Hydrogen Lyase-Overexpressing *Escherichia coli* Strains" Applied and Environmental Microbiology, Feb. 2006, p. 1716.
Japanese Office Action dated Nov. 2, 2010, issued in connection with Japanese Patent Application No. 2006-546734.

*Primary Examiner* — Yong Pak
(74) *Attorney, Agent, or Firm* — Nixon & Vanderhye P.C.

(57) ABSTRACT

The present invention provides a microorganism which possesses the formate dehydrogenase gene and hydrogenase gene and contains an exogenous transcription activator gene for formate hydrogen lyase system, characterized in that said microorganism shows the transcription activator for formate hydrogen lyase system highly expressed therein and shows an improved function to generate hydrogen from formic acid, and a process for producing hydrogen using the microorganism.
Utilization of the microorganism of the present invention enables the hydrogen production from an organic substrate to be accomplished on a practical, commercial scale. The hydrogen to be produced by the present invention, which is free of carbon monoxide being causative to poisoning of the electrode catalyst for fuel cells, is useful as a fuel for fuel cells.

11 Claims, 5 Drawing Sheets

US 8,728,791 B2

MICROORGANISM HAVING THE IMPROVED GENE FOR HYDROGEN GENERATION CAPABILITY, AND PROCESS FOR PRODUCING HYDROGEN USING THE SAME

This application is the US national phase of international application PCT/JP2005/022463 filed 7 Dec. 2005 which designated the U.S. and claims benefit of JP 2004-356084, dated Dec. 8, 2004, the entire content of which is hereby incorporated by reference.

FIELD OF THE INVENTION

The present invention relates to a microorganism which possesses the formate dehydrogenase gene and hydrogenase gene, contains an exogenous transcription activator gene (hereinafter referred to briefly as fhlA gene) for formate hydrogen lyase system (hereinafter referred to briefly as FHL system) and highly express said genes within the microorganisms. Furthermore, the present invention relates to the said microorganism which has inactivated the gene (hereinafter referred to briefly as hycA gene) for suppressing the formation of the FHL system to thereby enhance further the FHL system. Also, the present invention relates to a process for producing hydrogen with use of the said microorganism.

BACKGROUND ART

Hydrogen is an ultimate clean energy source which, unlike fossil fuels, is burnt without evolution of any substances that is liable to pose the environmental problem, such as carbon-dioxide gas and sulfur oxides, and, delivering a heat quantity per unit mass three times or more greater than petroleum oils, and when supplied to fuel cells, can be converted into electric and thermal energies with a high degree of efficiency.

As a conventional chemical process for production of hydrogen, for example, there have been proposed several technologies, inclusive of the thermal-cracking or steam reforming process of natural gas or naphtha. These production technologies need the severe reaction conditions of high temperature and high pressure, while they yield the synthesis gas containing CO (carbon monoxide), and such gas, on the occasion of utilization in fuel cells, is consequently required to be freed of CO to circumvent the problem of poisoning of fuel-cell electrode catalysts. However, the removal of CO involves technological difficulties, and is not easy to accomplish.

On the other hand, the method of biological hydrogen generation by microorganisms proceeds under the mild reaction conditions of ambient temperature and atmospheric pressure, and generates the gas, which does not contain CO, without being required to remove the same.

From such viewpoints, the method of biological hydrogen generation with use of microorganisms is attracting enhanced attention as a more preferred means of supplying a fuel intended for use in fuel cells.

The method of biological hydrogen generation is roughly classified into the two methods: the method using a photosynthetic microorganism and the method with use of a non-photosynthetic microorganism (mainly anaerobic microorganisms).

The former method, although it utilizes the energy of light for generation of hydrogen, needs a vast light-capturing surface area because of its low utilization efficiency of the light energy, and encounters lots of the problems left to be solved, such as the expensive cost investment requirement for the hydrogen generation facilities and difficulties in securing its maintenance, thus still remaining far from the commercially practical level.

With reference to the latter method, there have been known the various metabolic pathways being responsible for generating hydrogen by the anaerobic microorganisms. Such metabolic pathways include, for example, the pathway of generating hydrogen during the step of break-down of glucose to pyruvic acid; the pathway of generating hydrogen during the step of production of acetic acid from pyruvic acid via acetyl CoA; and the pathway of generating hydrogen directly from formic acid derived from pyruvic acid, and the like.

Among these, the pathway of generating hydrogen directly from formic acid derived from pyruvic acid is working by lots of microorganisms as the FHL system.

Referring to the FHL system, a report was published on *Escherichia coli*. With regard to the FHL system of *Escherichia coli*, however, there was proposed a model structural assembly indicating a complex consisting of numerous, extremely complex enzymatic proteins, but there has not yet been clarified the whole aspects of gene groups encoding the enzymatic proteins involved in generation of hydrogen (refer to Sauter, M., et al., Molecular Microbiology, 1992, vol. 6, p. 1523-1532).

With reference to the function of the FHL system, on the other hand, the fhlA gene has been analyzed to be identified as a transcription activator gene for the gene encoding part of the enzymatic proteins constructing the FHL complex (Schlensog, V., et al., Molecular Microbiology, 1990, vol. 4, p. 1319-1327).

The present invention also relates to a technique of inactivating the hycA gene. It was shown by Penfold, D. W. et al. (Enzyme and Microbial Technology, 2003, vol. 33, p. 185-189) that an *Escherichia coli* strain being deficient in the hycA gene exhibits an improved hydrogen-generation capability from saccharides, such as glucose, as compared with its wild strain, but no mention was made about the fhlA gene. There has not been known so far in the past that the microorganism, which possesses the FHL system having undergone to transformation in terms of the fhlA and hycA genes as identified in the present invention out of a group of the genes involved in the formation of the FHL system, or a conjugated body of complex enzymatic proteins, can acquire the outstandingly improved function to generate hydrogen from formic acid.

DISCLOSURE OF THE INVENTION

The Problem that the Invention is Intended to Solve

As a process for producing hydrogen with use of a microorganism from an organic substrate, heretofore, there has mainly been proposed a method for cultivating an anaerobic microorganism possessing the hydrogen-generation capability under anaerobic conditions. Namely, in such method, hydrogen is produced by proliferation of the anaerobic microorganism. However, such procedure shows a low hydrogen-generation rate per unit reaction volume, and is required of enhanced hydrogen-generation productivity per unit microbial cell in order to attain satisfactory hydrogen-production rate.

Under these circumstances, the present invention is aimed at materializing further enhancement of the hydrogen-generation productivity per unit microbial cell through strengthened production of the enzymes being involved in the generation of hydrogen from formic acid within the microbial cell by means of high expression of the fhlA gene as a function of the FHL system within the microorganism as used, and additionally through inactivation of the hycA gene.

Thus, the objectives of the present invention are to create a microorganism with a by far improved capability to generate hydrogen capability from formic acid, and to provide a process for producing hydrogen with use of such microorganism.

Means for Solving the Problems

The present inventors, with a specific view to solving the above-described problems, conducted intensive investigation, and as a result, created a microorganism which can highly express the fhlA gene owned by a microorganism possessing the formate dehydrogenase and hydrogenase genes, while they found that such created microorganism can generate hydrogen and shows a by far improved hydrogen-generation rate, as compared with the conventionally known ones. Such findings were followed by further research studies, leading to completion of the present invention.

Namely, the present invention relates to:

(1) A microorganism which possesses the formate dehydrogenase gene and hydrogenase gene and contains an exogenous transcription activator gene for formate hydrogen lyase system, characterized in that said microorganism shows the transcription activator for formate hydrogen lyase system highly expressed therein and shows an improved function to generate hydrogen from formic acid;

(2) The microorganism as described above under (1), characterized in that said microorganism has the gene for suppressing the formation of the formate hydrogen lyase system undergone inactivation;

(3) The microorganism as described above under (1) or (2), characterized in that said microorganism is a transformant of *Escherichia coli;*

(4) The microorganism as described above under (3), characterized in that *Escherichia coli* is *Escherichia coli* W3110 strain (ATCC 27325);

(5) *Escherichia coli* W3110/fhlA-pMW118 strain (International Patent Organism Depository Center, National Institute of Advanced Industrial Science and Technology, Accession No. FERM BP-10444);

(6) *Escherichia coli* W3110 ΔhycA/fhlA-pMW118 strain (International Patent Organism Depository Center, National Institute of Advanced Industrial Science and Technology, Accession No. FERM BP-10443);

(7) A process for producing hydrogen, characterized in that said process comprises cultivating a microorganism as described above under any one of (1) to (6) under aerobic conditions, followed by further cultivation under anaerobic conditions, and cultivating the said cultivated microorganism in a solution for hydrogen generation under feeding of an organic substrate;

(8) A process for producing hydrogen as described above under (7), characterized in that use is made of a carbon source with a slower rate of metabolism than glucose during cultivation under anaerobic conditions;

(9) A process for producing hydrogen as described above under (8), characterized in that the carbon source with a slower rate of metabolism than glucose is galactose or arabinose.

It is to be noted that as used in the present specification and claims, the symbol "ΔhycA" is understood to denote:

 [Chemical Formula 1]

The Effect of the Invention

The present invention can provide the microorganisms having an improved hydrogen-generation capability.

The present invention can permit the hydrogen generation from an organic substrate with use of a microorganism to be materialized on a commercial, practical scale. The hydrogen to be produced with the process for producing hydrogen according to the present invention, is free of CO (carbon monoxide) in the gas produced, unlike the counterparts as produced with chemical processes for production of hydrogen, and can consequently be suitably used as a fuel for fuel cells, without taking any means to remove the CO being attributable to poisoning of the electrode catalyst for fuel cells.

Furthermore, the process for producing hydrogen according to the present invention, which is feasible at ambient temperature, does not require the time for heating and cooling of the equipment, and enables the hydrogen production to be instantaneously initiated and ceased or suspended, respectively. Also, the process does not need external energy necessary for the said heating and cooling, and can produce hydrogen in the environmentally clean manner and at reduced products costs.

THE BEST MODE FOR CARRYING OUT THE INVENTION

Figure 1:
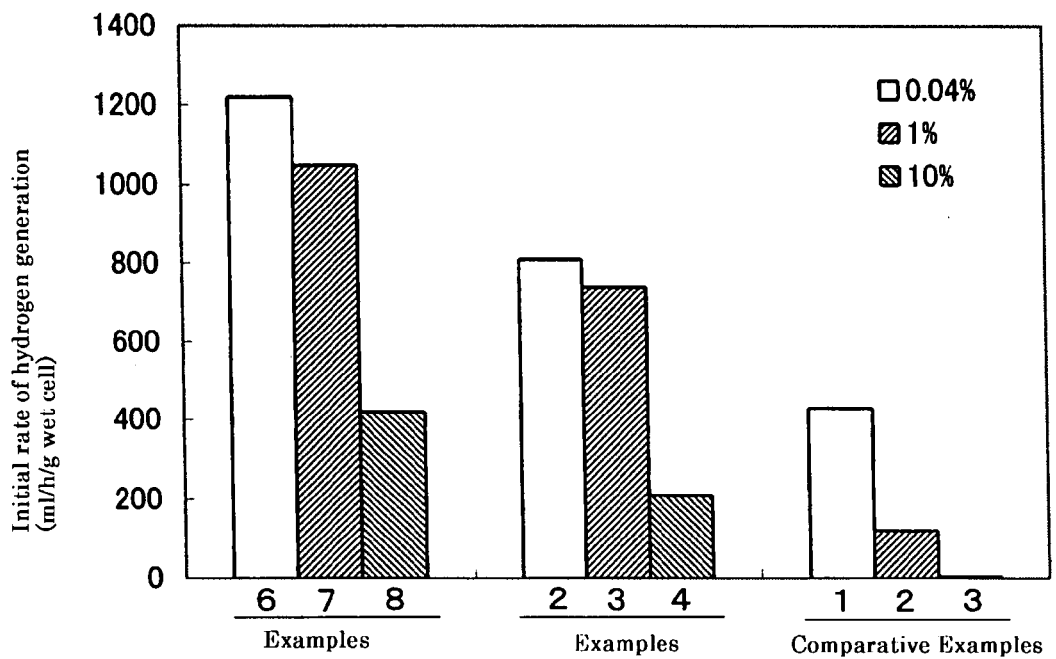
FIG. 1 is graphs showing the hydrogen-generation capabilities of the microorganisms as provided in Examples 1 and 5.

The microorganism to be used in the production of hydrogen of the present invention is preferably microorganisms which possess the formate dehydrogenase gene and hydrogenase gene, contain the exogenous fhlA gene and highly express said genes within themselves, or alternatively microorganism possessing the said exogenous gene which furthermore have the gene for suppressing the formation of the FHL system undergone inactivation and have the FHL system further strengthened. Cultivation of such microorganisms in a solution for hydrogen generation under feeding of an organic substrate can yield hydrogen in industrially favored manner. To be described below in detail is the present invention.

As used herein, the term "highly express" is understood to mean that the expressed amount or quantity of the objective gene is increased, and includes the cases where not less than two of the objective genes are possessed and where the expressed amount or quantity is increased through modification of the promoter, etc. even for only one of the objective gene owned by a microorganism.

The expression "suppress the formation of the FHL system" refers to inhibition or suppression of the formation of the FHL system which is a pathway for generating hydrogen from formic acid originating from pyruvic acid. It is to be noted that the above-described inhibition or suppression of the formation of the FHL system includes partial inhibition or suppression of the above-described pathway. The term "gene capable of suppressing the formation of the FHL system"

refers to all the genes associated with inhibition or suppression of the formation of the FHL system.

Also, the term "exogenous gene" refers to any genes which, originating in any microorganisms of the same or different species, are introduced anew into a host microorganism by means of a procedure of utilizing a vector, and the like. The term "inactivation" refers to inhibition or suppression of the expression of the objective gene, wherein said inactivation also includes the cases where the objective gene is deleted or defective by destruction of the gene, etc, with its expression being not observed. As used herein, the term "gene" or "DNA" is meant to comprehend not only double-stranded DNAs but also single-stranded DNAs, such as sense strand and antisense strand individually constituting such DNAs, whereby they are not particularly limited in terms of their length. The gene (DNA) as used herein, unless otherwise specified particularly, is accordingly understood to contain all of double-stranded DNAs, single-stranded DNAs (positive strands) comprising cDNA, and single-stranded DNAs (complementary strands) each having a strand complementary to the said positive strand, as well as fragments thereof. The said "gene" or "DNA" comprehends not only the "genes" or "DNAs" represented by the particularly specified base sequence (e.g., SEQUENCE LISTING ID NO: 13 or 14), but also "genes" or "DNAs" encoding proteins (e.g., homologues, variants and derivatives, etc.) equivalent in biological function to the proteins encoded by them. The "genes" or "DNAs" encoding such homologues, variants or derivatives can be specifically exemplified by "genes" or "DNAs" consisting of the base sequences which hybridize with the complementary sequences showing the said, particularly specified base sequences under the below-described stringent conditions. Also, the genes and DNAs can include, for example, expression-regulatory region or introns.

The parent strain to be used for the construction of the microorganism of the present invention preferably include the formate dehydrogenase gene (F. Zinoni, et al., Proc. Natl. Acad. Sci. USA, vol. 83, pp. 4650-4654, July 1986 Biochemistry) and hydrogenase gene (R. Boehm, et al., Molecular Microbiology, 4(2), 231-243 (1990)). The microorganism to use as the above-described parent strain is preferably anaerobic microorganisms. The anaerobic microorganism may be exemplified by obligatory or facultative anaerobic microorganisms. The anaerobic microorganism includes, for example, microorganisms of the genus *Escherichia*, such as *Escherichia Coli* ATCC9637, ATCC11775, ATCC4157, ATCC27325, etc.); microorganisms of the genus *Klebsiella*, such as *Klebsiella pneumoniae* (ATCC13883, ATCC8044, etc.); microorganisms of the genus *Enterobacter*, such as *Enterobacter aerogenes* (e.g., ATCC13048, ATCC29007, etc.); microorganisms of the genus *Clostridium*, such *Clostridium* beijerinckii (e.g., ATCC252752, ATCC17795, etc.), and the like. As the anaerobic microorganism, the facultative anaerobic microorganisms are more desirable than the obligatory anaerobic ones. Among the above-described microorganisms, *Escherichia coli* or *Enterobacter aerogenes* are more preferable.

The fhlA gene to be used in the present invention include, for example, the fhlA genes as obtained through literature survey on the fhlA gene or by the known molecular biological experiments, or as identified through search with use of databases described in URLs, such as DNA Data Bank of Japan (DDBJ; URL: gib.genes.nig.ac.jp) or Geno Base (ecoli.aist-nara.ac.jp/GB5/index.html) of Genomic analysis of E.coli in Japan. Also, the fhlA gene includes the genes having the base sequences showing not less than about 80% of homology with the ones of the genes as obtained in the above, whose DNAs encode the proteins exhibiting transcription activator activity for the FHL system. The base sequences, which show high homology with the one of the fhlA gene, can be identified through homology search with the databases described in URLs, such as DDBJ (ddbj.nig.ac.jp/search/blast-j.html).

Specific examples of the fhlA gene preferably include the fhlA gene of *Escherichia coli* K-12 W3110 strain. The base sequence of the fhlA gene of *Escherichia coli* K-12 W3110 strain has been registered at GenBank, and SEQUENCE LISTING ID No. 13 shows the base sequence of the fhlA gene of Escherichia coli K-12 W3110 strain as registered at GenBank.

The fhlA gene can be obtained for example by following a procedure similar to the ordinary gene cloning procedure while using as a template a chromosomal DNA of a microorganism exhibiting transcription activator activity for the FHL system. For example, the fhlA gene can be obtained by PCR (polymerase chain reaction) while using as a template the chromosomal DNA of *Escherichia Coli* K-12 W3110 strain and utilizing as a primer the oligonucleotides showing the base sequences as represented by SEQUENCE LISTING ID Nos. 1 and 2, and the like. The procedures for construction of the DNA library used in the gene cloning, hybridization, PCR, preparation of vectors, cleavage and ligation of DNA, transformation, etc. are described for example in Sambrook, J., Fritsch, E.F., Maniatis, T., Molecular Cloning, Cold Spring Harbor Laboratory Press, 1.21 (1989), and the like. The fhlA gene can also be synthesized based on the base sequence of the fhlA gene as obtained in the above by use of the DNA synthesizer, etc.

In the present invention, the procedure of introducing the thus-obtained fhlA gene into an anaerobic microorganism of the above-mentioned parent strain includes, for example, a procedure which involves inserting the fhlA gene (DNA) or a DNA having a native promoter or an exogeneous promoter, such as T7, lac, tac or trc, upstream of the said DNA into a vector, such as plasmid or cosmid, and introducing the vector having the said DNA inserted into the microorganism (hereinafter referred to in some instances as a host) of the parent strain. The said vector may include the ribosome-binding site, initiation codon, termination codon or terminator, etc., as the case may be. Miscellaneous procedures include a procedure which consists of inserting the fhlA gene into a transposon, followed by insertion into the chromosome of a host, and the like. The above-described fhlA gene (DNA) includes DNAs which hybridize with said fhlA gene (DNA) under stringent conditions and encode the protein exhibiting transcription activator activity for the FHL system. The DNA, which undergoes hybridization under stringent conditions, refers to DNAs which can be obtained by use of the colony hybridization procedure, plaque hybridization procedure or southern blot hybridization procedure, etc. while utilizing the said DNA as a probe. Particularly, there can be mentioned, for example, the DNAs which can be identified by performing hybridization at a temperature in the neighborhood of ca. 65° C. under the presence of sodium chloride of a concentration in the range of ca. 0.7 to 1.0M with use of a filter having DNA of a colony or plaque origin immobilized, and then washing the filter at a temperature in the neighborhood of ca. 65° C. with use of SSC solution (SSC solution of a 1-fold concentration shows the composition consisting of 150 mM of sodium chloride and 15 mM of sodium citrate) of a concentration in the range of ca. 0.2 to 2-fold.

As the above-described vector, it is preferable to use plasmids. The use of plasmids can facilitate the fhlA gene to be highly expressed in the above-described anaerobic microorganisms. The type of plasmids to be used is not particularly limited, and any plasmids can be preferably used, only if they are, for example, autonomously replicable plasmids in *Escherichia coli*. Specific examples of said plasmids include pUC19, pUC18 (both produced by Takara-Bio CO. of Japan), pHSG298, pHSG299, pHSG398, pHSG399 (all produced by Takara-Bio Co. of Japan), low-copy plasmid pMW219, pMW218, pMW119, pMW118 (all produced by Nippon Gene CO. of Japan), pTrc99A (produced by Roche Diagnostics Co.) having trc promoter, and the like.

Insertion of the above-described DNA into a vector (plasmid) can be performed by the per se known procedures, but it is simple and practical to use the commercially available ligation kits. Such ligation kits include, for example, DNA Ligation Kit ver 1 (produced by Takara-Bio Co. of Japan), DNA Ligation kit ver 2.1 (produced by Takara-Bio Co. of Japan), Fast-Link (registered trademark), DNA Ligation Kit (produced by AR BROWN Co., LTD.), Ligation-Convenience Kit (produced by Nippon Genes Co. of Japan) or Rapid DNA Ligation Kit (produced by Roche-Diagnostics Co.), etc.

Insertion of the vector as obtained by the above-described procedure into a host can be performed by the per se known procedures. The said procedure includes, for example, the procedure which comprises treating the competent cells with calcium chloride (Mandel, M. and Higa, A., J. Mol. Biol., 53, 159 (1970)), the procedure which involves introducing into the cell as converted in the form of a protoplast or spheroplast (Chang, S, and Choen, S. N., Molec. Gen., Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)), electroporation method (Canadian Journal of Microbiology, 43, 197 (1997)), and the like.

The microorganism, which has had the fhlA gene introduced therein, can be easily selected, for example, by the known selection procedures by means of blue/white colonies screening by X-gal or drug-resistance markers (e.g., genes provided with antibiotic resistance, such as ampicillin resistance gene, streptomycin_resistance gene, kanamycin resistance gene, neomycin resistance gene, etc.), and the like.

High expression of the fhlA gene can also be achieved by allowing the fhlA gene to exist on the chromosomal DNA of the microorganism of the above-mentioned parent strain, in many copies. Miscellaneous procedures of allowing high expression of the fhlA gene preferably include a procedure of inactivating the hycA gene.

As the procedure of inactivating the hycA gene, there may be mentioned, for example, non genetic-engineering procedures through mutagenesis with use of a mutagen, and a procedure of introducing into a host the gene which has been allowed to undergo a genetic-engineering procedure of arbitrarily manipulating the gene sequence with use of the above-described restriction enzyme/ligase, and the like. In order to ensure that the hycA gene is inactivated in a host, it is preferable to inactivate the hycA gene by a genetic engineering procedure. The procedure of inactivating the hycA gene by a genetic engineering procedure includes, for example, a procedure which involves allowing the particularly determined site of the in-advance cloned objective gene to undergo mutation by a non genetic-engineering or genetic-engineering procedure, a procedure which comprises providing a defect site of the specifically determined length by a genetic engineering procedure, and a procedure which consists of preparing the DNA for inactivation of the objective gene by introducing an exogenous gene, such as a drug resistance marker, then introducing the DNA containing such variant gene into a host, and causing homologous recombination to inactivate the objective gene.

The hycA gene includes, for example, the hycA gene as obtained through literature survey or by the known biological experiment, or the hycA gene which can be identified through search for the databases described in URLs, such as DDBJ or GenoBase of Genomic Analysis of *E. coli* in Japan. Also, the hycA gene includes the genes having the base sequences showing not less than about 80% of homology with the ones of the genes as obtained in the above, whose DNAs encode the proteins for suppressing the formation of the FHL system.

Specific examples of the hycA gene to be used in the present invention preferably include the hycA gene of *Escherichia Coli* K-12 W3110 strain, whose base sequence has been registered at GenBank. The base sequence of the hycA gene of *Escherichia Coli* K-12 W3110 strain as registered at GenBank is shown in SEQUENCE LISTING ID. No. 14.

The hycA gene can be obtained for example by following a procedure similar to the ordinary gene cloning procedure while using as a template a chromosomal DNA of a microorganism possessing the FHL system. For example, the hycA gene can be obtained by PCR while using as a template the chromosomal DNA of *Escherichia Coli* K-12 W3110 strain and utilizing as a primer the oligonucleotides showing the base sequences as represented by SEQUENCE LISTING ID. Nos. 5 and 6, and the like. The procedures for construction of the DNA library used in the gene cloning, hybridization, PCR, preparation of vectors, cleavage and ligation of DNA, transformation, etc. are similar to those as described for the fhlA gene. The hycA gene can also be synthesized based on the base sequence of the hycA gene as obtained in the above by use of the DNA synthesizer, etc.

Also, the hycA gene (DNA) includes the DNAs which hybridize with the said hycA gene (DNA) under stringent conditions and encode the proteins for suppressing the formation of the FHL system. The stringent conditions are the same the conditions as described above for the fhlA gene (DNA).

In the present invention, the procedure of inactivating the hycA gene within the microorganism of the above-mentioned parent strain includes, for example, a procedure which involves inserting DNA (hereinafter referred to briefly as hycA/add), in which an exogenous gene, such as drug resistance marker gene (e.g., ampicillin resistance gene, streptomycin resistance gene, etc.) is inserted into the base sequences of the hycA gene, into a vector, such as plasmid or cosmid, and then introducing the vector having the said hycA/add into a host (i.e., the anaerobic microorganism of the parent strain or transformant microorganisms having the fhlA gene introduced), and the like. Insertion into a vector of the above-described hycA/add, introduction into a host of the said vector, and the like can be carried out by procedures similar to the procedure of allowing high expression of the above-described fhlA gene.

Selection of the host transformed with hycA/add can ordinarily be done by taking as an index the drug resistance marker gene inserted into the base sequence of the hycA gene. Specifically, the host transformed with hycA/add can be selected, for example, by culture on a medium containing a drug (e.g., ampicillin, streptomycin, etc.). Contrarily, an exogenous gene, such as a drug resistance marker gene, causes in some instances effects over genes in the neighborhood of the hycA gene having the exogenous gene inserted, resulting failure to transform the microorganism with hycA/add. In such cases, it is desirable to insert the drug resistance marker gene being provided with a defect site of the particularly determined length. Even if the gene, which has inserted the drug resistance marker gene being provided with a defect site of the particularly determined length, is allowed to express to produce the protein, however, such microorganism loses the drug resistance function and cannot survive on a medium containing the drug, and the drug resistance marker gene being provided with a defect site cannot act as a marker anymore. In such case, it is preferable to insert a lethal gene, etc. concurrently with the drug resistance marker gene being provided with a defect site to allow the homologous recombination. The lethal gene includes, for example, sacB gene originating from *Bacillus subtilis* which acts lethal in *Escherichia coli*, and the like. The procedure of performing the said homologous recombination is preferably carried out in the below-described manner. In the first place, there is prepared a vector which contains the DNA having an exogenous gene (e.g., drug resistance marker gene, etc.) to inactivate the hycA gene provided with a defect site of the particularly determined length and sacB, and such vector is introduced into a host to be allowed to undergo recombination to perform homologous recombination within the host. In order to perform the homologous recombination efficiently, it is more preferable to use a temperature-sensitive vector. The temperature-sensitive vector may be exemplified by pMA2, pLOI2226, pTH18ks1 or pTH18ks5 possessing the temperature-sensitive replicon pSC101ts. In the host having once-undergone to homologous recombination, the gene having the hycA gene inactivated coexists with the originally existing hycA gene (the non-inactivated hycA gene), and the successive cultivation under such conditions as may induce the lethal gene causes the lethal gene region and the non-inactivated gene region for suppressing the formation of the FHL system to be deleted through the second homologous recombination, resulting in inactivation of the hycA gene to thereby permit creation of the genetic recombinant strain capable of highly expressing the objective fhlA gene.

To be described below is a process for producing hydrogen with use of the microorganism obtained by the above-described procedures.

The process for producing hydrogen according to the present invention, which can be conducted into practice by cultivating the microorganism of the present invention under anaerobic conditions under feeding of an organic substrate, can preferably be carried out in accordance with a process consisting of three steps.

The first step is preferably a step of cultivating the microorganism under aerobic conditions. In this step, there is obtained a microorganism not possessing the hydrogen generation capability. The second step is preferably a step of converting the microorganism not possessing the hydrogen generation capability as obtained in the first step into a microorganism possessing the hydrogen generation capability. The third step is preferably a step of producing hydrogen with use of the microorganism possessing the hydrogen generation capability obtained in the second step.

The microorganism of the present invention can exhibit by far improved hydrogen-generation capability per microbial cell, as compared with the microorganisms which are not allowed to undergo genetic engineering treatment.

The cultivation under aerobic conditions in the first step is to be firstly described. In this step, it is feasible to cultivate the microorganism to high concentrations for a shortened period of time. As a means of cultivation, use is made of the known procedures. Such cultivation includes, for example, liquid culture, such as shake culture, jar-fermenter culture or tank culture, or solid culture. The cultivation temperature can be appropriately altered in such a range as may keep the transformant growing, but is ordinarily ca. 15 to 40° C., preferably ca. 30 to 40° C. The pH value of the medium is preferably in the range of ca. 6 to 8, while the cultivation time varies depending upon the cultivation conditions and ordinarily is preferably ca. 1 to 5 days.

To be next described is the second step of converting the microorganism not possessing the hydrogen generation capability to a microorganism possessing the hydrogen generation capability.

The conversion of the microorganism not possessing the hydrogen generation capability to the one possessing the hydrogen generation capability is preferably carried out by cultivation under anaerobic conditions. Cultivation under anaerobic conditions is preferably stirring or shake culture. The microorganism concentration at the time initiation of stirring or shake culture under anaerobic conditions is preferably ca. 0.01 to 80% by mass (relative to the mass of wet microbial cell). On the occasion of this, it is preferable to allow the microorganism to divide and proliferate during cultivation under anaerobic conditions in order for the microorganism to acquire the hydrogen generation capability, but the division and proliferation are not necessarily essential; the microorganism may not divide and proliferate, only if it can produce hydrogen in the FHL system of the present invention.

Under such anaerobic conditions, the oxidation-reduction potential of the culture liquid is desirably in the range of ca. −100 to −500 mV, preferably in the range of ca. −200 to −500 mV. As a procedure of adjusting the anaerobic conditions of the culture medium, any procedures may be preferably employable insofar as they remove dissolved oxygen in the culture medium, and include, for example, a procedure of removing dissolved gases by heat treatment or in-vacuo treatment of the culture medium or by bubbling through the culture medium with nitrogen gas, etc., and the like. As the specific procedure of removing dissolved oxygen in the culture liquid, a degassing treatment can be carried out under reduced pressure of not more than about $13.33 \times 10^2$ Pa, preferably not more than ca. $6.67 \times 10^2$ Pa, more preferably not more than ca. $4.00 \times 10^2$ Pa, for a period of time in the region of ca. 1 to 60 minutes, more preferably ca. 5 to 60 minutes, to obtain the culture liquid usable for cultivation under anaerobic conditions. Alternatively, a reducing agent may be added to the culture liquid, as the case may be, to prepare the culture liquids under anaerobic conditions. The reducing agent to be used includes, for example, thioglycolic acid, ascorbic acid, cysteine hydrochloride, mercaptoacetic acid, thiol acetic acid, glutathion or sodium sulfide, etc. These may be added to the culture liquid singly or in combination of several kinds.

In the cultivation to impart the hydrogen generation capability to the microorganism of the present invention under anaerobic conditions, use can be made of ordinary nutrient media containing a carbon source, nitrogen source, mineral source and the like. The carbon source may be exemplified by glucose, fructose, galactose, mannose, lactose, sucrose, arabinose, xylose, ribose, ribitol, arabitol, rhamnose, fucose, cellulose, molasses or glycerol, etc. Especially, use of the carbon sources showing a slower metabolic rate than glucose can permit the hydrogen generation capability to be imparted to the microorganism efficiently, and is preferable. The carbon source showing a slower metabolic rate than glucose may be preferably exemplified by lactose, galactose, arabinose, xylose, ribose, ribitol, arabitol, rhamnose, fucose, etc., with galactose and arabinose, among others, being more preferable. As the nitrogen source, there may be mentioned, for example, inorganic-form nitrogen source (e.g., ammonia, ammonium salt or nitrates, etc.) or organic-form nitrogen source (e.g., urea, amino acids or proteins, etc.), and the like. The above-mentioned carbon and nitrogen sources can be used singly or as an admixture, respectively. Both of the inorganic-form and organic-form nitrogen sources can be utilized similarly. As the mineral source, there may be mentioned, for example, K, P, Mg or S, etc. As the mineral source, inorganic salts can be preferably used, and there can be used, for example, potassium monohydrogen phosphate or magnesium sulfate, etc. If necessary, furthermore, there can also be added peptone, meat extract, yeast extract, corn steep liquor, casamino acid or nutrients, such as various vitamins inclusive of biotin or thiamine, etc. The culture medium preferably contains trace metal components for generation of hydrogen in the FHL system consisting from the formate dehydrogenase and the hydrogenase. Required trace metal components vary depending on the species of the microorganism to be cultured, and include, for example, iron, molybdenum, selenium or nickel, etc. These trace metal components are contained in significant quantities in natural nutrients, such as yeast extract and the like, and in culture media containing the natural nutrition sources, addition of trace metal components is not always necessary.

Referring to the microorganism concentrations, preferred use can be made of about 1 to 50% by mass (relative to the mass of the wet microbial cell). Especially, it is preferable to cultivate the microorganism at microorganism concentrations in the range of ca. 1 to 30% by mass under anaerobic conditions so as to enhance the hydrogen generation capability per unit microbial cell.

With reference to the conditions for stirring or shake culture under anaerobic conditions, the temperature range desirably is ca. 20 to 45° C., and preferably ca. 25 to 40° C., while the pH range is preferably pH ca. 4.0 to 10.0, and more preferably pH ca. 5.0 to 8.0. It is preferable to control the pH simultaneously, and it is also possible to adjust the pH_using an acid or alkali. Both the above-mentioned temperature and pH ranges are optimum for the microorganism of the present invention. Ordinarily, the carbon-source concentration at the initiation of cultivation is preferably ca. 0.1 to 20% (w/v) and still more preferably ca. 1 to 5% (w/v).

Then, there is to be described below the detailed conditions for the third step of generating hydrogen.

After completion of the second step of the cultivation for imparting the hydrogen generation capability, the microorganism possessing the hydrogen generation capability, as present in the culture medium, can be used as such or after being once separated, followed by addition of the separated microorganism to the solution for generating hydrogen left in the reductive condition. In both of these cases, an organic substrate can be supplied to the culture medium or the solution for generating hydrogen to thereby make the microorganism generate hydrogen.

The procedure of generating hydrogen includes, for example, a procedure (direct supply method) of supplying continuously or intermittently an organic substrate, such as formic acids, or a procedure (indirect supply method) of supplying compounds of saccharides susceptible to conversion to formic acids in the metabolic pathways within the microorganism, and the like. The above-described direct and indirect supply methods can be used concomitantly in combination. The organic substrate to be supplied to the above-mentioned medium or solution for generating hydrogen may be preferably exemplified by formic acids, etc.

In this context, formic acids refer to substances having a hydrocarboxyl group (the chemical structure: $HCOO^-$), and their specific examples include formic acid, sodium formate, potassium formate, calcium formate, manganese formate, nickel formate, cesium formate, barium formate or ammonium formate, etc. Among these, formic acid, sodium formate, potassium formate, calcium formate or ammonium formate is preferred in terms of increased solubility in water, and formic acid, sodium formate or ammonium formate is more preferable in terms of reduced costs. The concentration of formic acid as an organic substrate is preferably not less than ca. 20% (w/w), preferably not less than ca. 30% (w/w). Specifically, when formic acid is used as an organic substrate, for example, the concentration is preferably ca. 30 to 100% (w/w), still more preferably ca. 50 to 100% (w/w). Lowered concentrations of formic acids are not preferred, for the reason of the fact that lowered concentrations bring about increases in volume of the solution for generating hydrogen according to progresses in supply of formic acids, resulting in eventual dilution and alteration of the microorganism concentration. As for the rate of supplying the organic substrate, the range of the rate is not especially limited, only if the pH of the solution for generating hydrogen is controlled within the range of about 4.0 to 9.0.

The reaction temperature for the hydrogen generation reaction varies depending upon the species of microorganism as used, and generally is preferably in the range of ca. 20 to 45° C. for use of ambient-temperature microorganisms, still more preferably in the range of ca. 30 to 40° C. from the viewpoint of preservation of the microorganism's life.

As the solution for generating hydrogen, use is required to be made of a solution for generating hydrogen maintained under the reductive state. Referring to the anaerobic conditions of this solution, the solution for the hydrogen generation preferably shows an oxidation-reduction potential of ca. $-100$ to $-500$ mV, and still more preferably ca. $-200$ to $-500$ mV.

The microorganism concentration of the solution for generating hydrogen is ca. 0.1 to 80% by mass (relative to the mass of wet microbial cell), preferably ca. 0.1 to 70% by mass (relative to the mass of wet microbial cell), still more preferably ca. 10 to 70% by mass (relative to the mass of wet microbial cell).

Since the gas evolves vigorously, it is preferable to add a defoaming agent to the solution for the hydrogen generation. As a defoaming agent, use can be made of the known ones, and specifically, there are preferably used silicone based ones (e.g., SI (Silicone), etc.) or polyether based ones (e.g., PE-H (Polyether-High), PE-M (Polyether-Medium), PE-L (Polyether-Low), etc.).

To be described below is the fuel cell system using the process for producing hydrogen according to the present invention. The electric current can be produced by putting the microorganism according to the present invention into the device called a microorganism fuel cell.

In the process for producing hydrogen according to the present invention, there is generated the gas composed mainly of hydrogen and carbon dioxide, and carbon monoxide in principle is not produced. In utilizing a fuel for a currently available solid polymer electrolyte type of fuel cells, generally, it is necessary to use a system (CO transformer, CO eliminator, etc.) for removing carbon monoxide to thereby maintain the CO level at not more than 10 ppm. In the system utilizing as a fuel for fuel cells the process for producing hydrogen according to the present invention, there is not produced CO, thus eliminating the need for the CO-removal system, and the equipment can be simplified.

In the process for producing hydrogen according to the present invention, it is easy to conduct temperature controlling of the reaction vessel during production of hydrogen. For example, the conventional process for generating hydrogen from natural gas requires the temperature condition of not less than about 600° C., while even utilization of methanol necessitates the temperature condition up to several hundred degree Centigrades, whereas the reaction vessel in the process for producing hydrogen according to the present invention may be preferably maintained at the temperature condition of ambient temperature. In the process for producing hydrogen according to the present invention, consequently, the length of time required for temperature raising or cooling is not needed any more, and the hydrogen generation or cessation can be done immediately, if such necessities arise.

EXAMPLES

The present invention is to be described below more specifically by way of examples, but the present invention is not understood to be limited thereto.

Example 1

Construction Of A Strain Of *Escherichia coli* (The Strain Capable Of Highly Expressing The Transcription Activator fhlA for the fhl System)

1) Extraction of the Genome DNA

*Escherichia coli* W3110 strain (ATCC27325) was subjected to shake culture in 10 mL of the LB culture medium (Luria-Bertani culture medium) as described in Table 1 at 37° C. overnight, and the genome DNA was extracted using GenomicPrep Cells and Tissue DNA Isolation Kit (produced by Amersham Bioscience).

TABLE 1

| Composition ingredients | Ingredient amount |
|---|---|
| Water | 1000 ml |
| Tryptone | 10 g |
| Yeast extract | 5 g |
| Sodium chloride | 5 g |

2) Preparation of the Vector

From the genome DNA obtained under 1) as described above, the fhlA and the promoter region upstream thereof were amplified with use of a thermal cycler, Gene Amp PCR System 9700 (produced by ABI), while using the below-described primers.

```
GGGGTACCTAAAATTCTAAATCTCCTATATGTTAG  (SEQ ID NO: 1)

CGGGATCCTGCGTCATCTCATCGATGACAA       (SEQ ID NO: 2)
```

Figure 3:
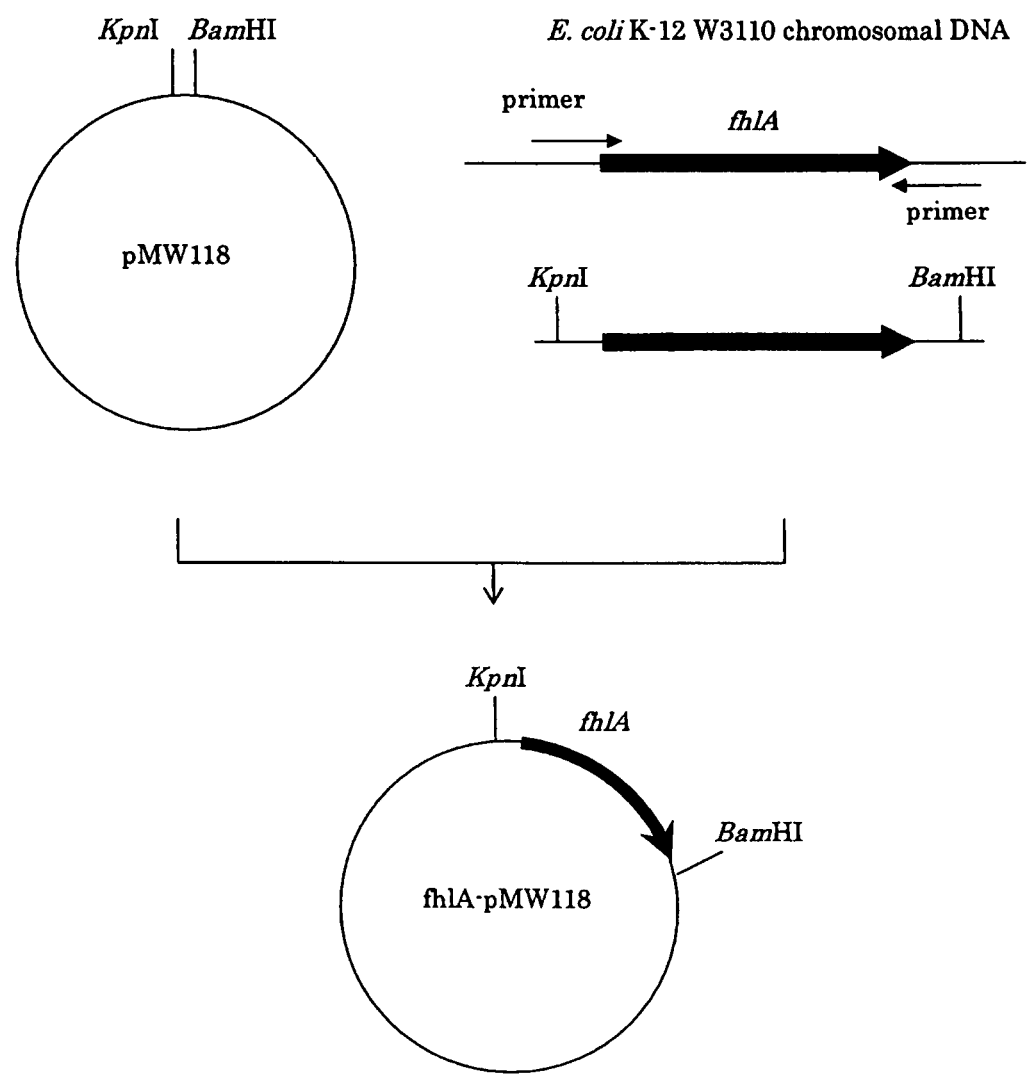
FIG. 3 is a schematic view showing the construction of the vector fhlA-pMW118 of Example 1.

The amplified DNA and plasmid pMW118 (produced by Nippon Gene Co. of Japan) were restriction-enzyme treated with KpnI, BamHI, followed by ligation with use of DNA Ligation Kit ver 2.1 (produced by Takara Shuzo CO. of Japan) to give the vector fhlA-pMW118, whose construction is illustrated in FIG. 3.

3) Introduction of the Vector and Preparation of the Strain Capable of Highly Expressing fhlA The vector fhlA-pMW118 obtained under 2) as described above was introduced into *Escherichia coli* W3110 strain through the electroporation procedure, followed by cultivation in the culture medium (LB agar medium containing ampicillin) as described in Table 2 to give a colony of the objective strain capable of highly expressing fhlA.

TABLE 2

| Composition ingredients | Ingredient amount |
|---|---|
| Water | 1000 ml |
| Tryptone | 10 g |
| Yeast extract | 5 g |
| Sodium chloride | 5 g |
| Ampicillin | 50 mg |
| Agar | 15 g |

4) Molecular-Biological Identification of the Strain Capable of Highly Expressing fhlA Evaluation of the strain capable of highly expressing fhlA of *Escherichia coli* W3110 strain as obtained by the above-described procedure was conducted by the real-time RT-PCR method. The real-time RT-PCR method was carried out by following the below-described procedure; in the first place, the strain capable of highly expressing fhlA and the wild strain were cultivated in the LB medium as described in Table 1 being supplemented with 20 mM of glucose (furthermore 50 mg/L of ampicillin for the strain capable of highly expressing fhlA) anaerobically for 10 hours, and the total RNA was extracted from the resultant microbial cells with use of RNeasy Mini Kit (produced by QUIAGEN Co.). The total RNA, the below-described primer for fhlA:

```
Fwd: AGATCGTTTCTGTCGTCACCG    (SEQ ID NO: 3)

Rev: CCGGCATAACAACTCATAGTCG   (SEQ ID NO: 4)
``` and QuantiTect SYBR Green RT-PCR (produced by QIAGEN Co.) were used to prepare a solution mixture as described in Table 3, followed by reverse transcription with use of ABI Prism 7000 Sequence Detection System (produced by ABI Co.) at 50° C. for 30 min, and thermal denaturation at 95° C. for 15 min, and DNA was synthesized by thermal cycle of 40 cycles under the conditions of 95° C. for 15 sec.→57° C. for 20 sec.→60° C. for 1 min. The difference in expression of fhlA was examined from the difference in CT value as calculated from the DNA amplification curve through time-course monitoring of DNA amplification by PCR, coupled with detection of the fluorescence intensity at each cycle. As a result, it was confirmed that the strain capable of highly expressing fhlA exhibits more than 2-fold fhlA expression amount that of the wild strain.

TABLE 3

Table of real-time RT-PCR composition

| Composition ingredients | Ingredient amount |
|---|---|
| Total RNA | 50 ng |
| Primer (Fwd) | 0.5 µM |
| Primer (Rev) | 0.5 µM |
| RT Mix | 0.5 µl |
| 2 x Master Mix | 25 µl |
| Total | 50 µl |

As described above, the *Escherichia coli* W3110 strain transformed with the vector fhlA-pMW118 was named *Escherichia coli* W3110/fhlA-pMW118 and has been deposited at international Patent Organism Depositary, National institute of Advanced science and Technology of Japan (under Accession No: FERM BP-10444).

Examples 2 to 4

Process for Producing Hydrogen with Use of *Escherichia coli* W3110 Strain (The Strain Capable Of Highly Expressing The fhla Gene) As Obtained in Example 1

1) Cultivation Under Aerobic Conditions

Escherichia coli W3110 strain (the strain capable of highly expressing the fhlA gene) was subjected to shake culture in 10 mL (Example 2), 200 mL (Example 3) and 2000 mL (Example 4) of the culture liquid having the composition as shown in Table 1 being supplemented with 50 mg/L of ampicillin overnight at 37° C. under aerobic conditions.

2) Cultivation Under Anaerobic Conditions for Imparting the Hydrogen Generation Capability to the Microorganism Then, the microorganism, which was yielded by subjecting the culture broth as obtained by shake culture overnight under aerobic conditions to a centrifuge (5,000 rpm, for 15 min) and removing the resultant supernatant liquid, was cultivated in 200 mL of the culture liquid having the composition as shown in below Table 4 at 37° C. for 24 hours (Example 2) or 12 hours (Examples 3 and 4) so as to produce the microorganism possessing the hydrogen generation capability. On this occasion, cultivation under anaerobic conditions was initiated while setting the microorganism concentration at 0.04% by mass (Example 2), 1% by mass (Example 3) and 10% by mass (Example 4) relative to the mass of wet microbial cell, respectively, whereby 5N sodium hydroxide was added timely to maintain the pH at 6.0.

TABLE 4

| Composition ingredients | Ingredient amount |
|---|---|
| Water | 1000 ml |
| Yeast extract | 0.5% (by mass) |
| Tryptonpepton | 1.0% (by mass) |
| Sodium molybdate | 10 μM |
| Sodium selenite | 10 μM |
| Disodium hydrogenphosphate | 26.5 mM |
| Sodium dihydrogenphosphate | 73.5 mM |
| Glucose | 120 mM |
| Sodium sulfide | 200 mM |
| Ampicillin | 50 mg |

3) Investigation on the Hydrogen Generation Capability

The microorganism as cultivated under the conditions as described above under 2) was separated by centrifugation, and suspended in 50 mL of the solution for generating hydrogen having the composition as shown in below Table 5 (about 0.2% by mass of the microorganism concentration, relative to the mass of wet microbial cell; hereinafter referred to as "microorganism-suspended solution for generating hydrogen").

TABLE 5

| Composition ingredients | Ingredient amount |
|---|---|
| Water | 1000 ml |
| Yeast extract | 0.5% (by mass) |
| Tryptonpepton | 1.0% (by mass) |
| Sodium molybdate | 10 μM |
| Sodium selenite | 10 μM |
| Disodium hydrogenphosphate | 26.5 mM |
| Sodium dihydrogenphosphate | 73.5 mM |
| Defoaming agent | 0.01% (by mass) |

The microorganism-suspended solution for generating hydrogen as prepared in the above was admixed with sodium formate to 100 mM of the concentration of sodium formate to thereby measure the hydrogen generation capability of the microorganism.

The method of measuring the hydrogen generation capability of the microorganism was carried out by collecting by the method of replacement over the water the gas evolved immediately after dropwise addition of sodium formate. The initial rate of hydrogen generation was determined on the basis of the volume of the gas evolved for 30 sec from addition of sodium formate. Analysis of the evolved gas by gas chromatography (manufactured by Shimadzu Co. of Japan) revealed that the gas contained 50% by volume of hydrogen and the remaining volume of gas (carbon dioxide).

The results are shown in FIG. 1.

Example 5

Preparation of Escherichia coli w3110 strain being capable of highly expressing the fhla gene and having the hyca gene disrupted 1) Extraction of the Genomic DNA Escherichia coli W3110 strain (ATCC 27325) was subjected to shake culture in 10 mL of the LB medium as described in Table 1 at 37° C. overnight, followed by extraction of the genomic DNA with use of GenomicPrep Cells and Tissue DNA Isolation Kit (Amersham bioscience Co.).

2) Preparation of the Vector to Prepare the Strain Having the hycA Disrupted

From the genomic DNA obtained under 1) as described above, the hycA region was amplified using the below-described primers with use of a thermal cycler, GeneAmp PCR System 9700 (produced by ABI Co.).

CTCTGGATCCATTTCATCTTCGGGCGTGC  (SEQ ID NO: 5)

CTCTGAGCTCAAAGGTCACATTTGACGGCG  (SEQ ID NO: 6)

The amplified DNA and plasmid pHSG398 (produced by Takara Shuzo Co. of Japan) were restriction-enzyme treated with BamHI, SacI, followed by ligation with use of DNA Ligation Kit ver 2.1 (manufactured by Takara Shuzo Co. of Japan) to give the vector hycA-pHSG398. Furthermore, the resultant vector was restriction-enzyme treated with AvaII, XmnI, followed by blunt-end treatment with use of DNA Blunting Kit (manufactured by Takara Shuzo Co. of Japan) and subsequent ligation with EcoRI linker of 8 bp, GGAATTCC to give ΔhycA-pHSG398.

The sacB region, as amplified from pMV5 (Vertes, A. A. et al., Isolation and Characterization of IS31831, a transposable element from Corynebacterium glutamicum, Mol. Microbiol. 11, 739-746 (1994)) by PCR using the below-described primers,

CTCTGCATGCAACCCATCACATATACCTGC  (SEQ ID NO: 7)

CTCTGCATGCATCGATCCTCTAGAGTATCG  (SEQ ID NO: 8)

and plasmid pTH18ks1 (Hashimoto-Gotoh, T. et al., A set of temperature sensitive-replication/-segregation and temperature resistant plasmid vectors with different copy numbers and in an isogenic background (chloramphenicol, kanamycin, lacZ, repA, par, polA), Gene 241, 185-191 (2000)), as restriction-enzyme treated with BamHI, SphI, were ligated through ligation to give the vector sacB-pTH18ks1. The resultant vector sacB-pTH18ks1 was subjected to insertion of the ΔhycA region of ΔhycA-pHSG398 at the BamHI, SacI site to give the vector ΔhycA-sacB-pTH18ks1.

Figure 4:
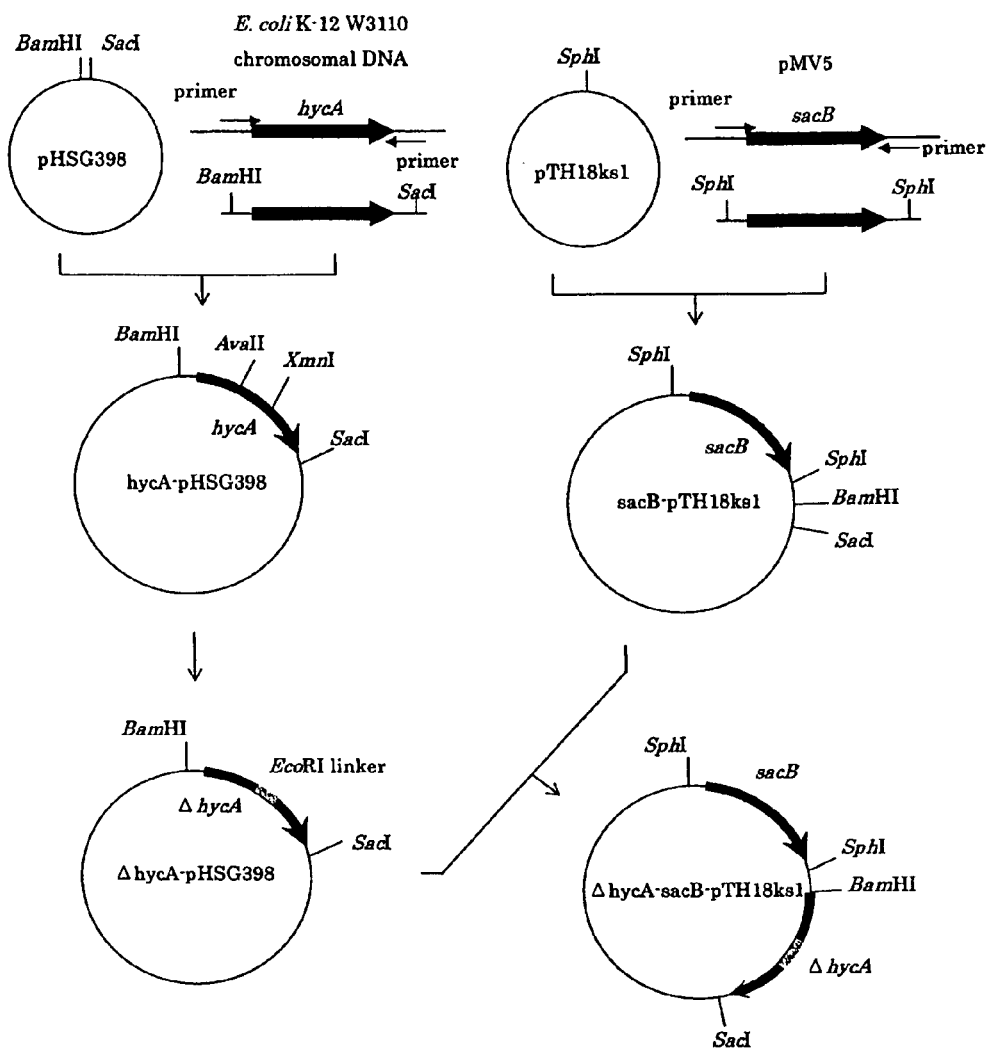
FIG. 4 is a schematic view showing the construction of the vector ΔhycA-sacB-pTH18ks1 of Example 5.

The construction of the vector is shown in FIG. 4.

3) Introduction of the Vector and Preparation of the Strain Having hycA Disrupted The vector ΔhycA-sacB-pTH18ks1 as obtained by the above-described procedure was introduced into Escherichia coli W3100 strain through the electroporation method. Cultivation was performed in the culture medium having the composition shown in Table 6 at 43° C. to allow homologous recombination, and there was obtained the recombinant strain having the vector inserted onto the chromosome of *Escherichia coli* W3110 strain.

TABLE 6

Composition of the culture medium
(LB medium containing kanamycin)

| Composition ingredients | Ingredient amount |
|---|---|
| Water | 1000 mL |
| Tryptone | 10 g |
| Yeast extract | 5 g |
| Sodium chloride | 5 g |
| Kanamycin | 50 mg |

After cultivation in the medium having the composition as described in above Table 6, the resultant strain was cultivated in the medium as shown in Table 7 at 30° C. to give the *Escherichia coli* W3110 strain having the hycA gene disrupted.

TABLE 7

Composition of the culture medium (minimal medium containing sucrose)

| Composition ingredients | Ingredient amount |
|---|---|
| Water | 1000 ml |
| Potassium dihydrogenphosphate | 2 g |
| Dipotassium hydrogenphosphate | 7 g |
| Ammonium sulfate | 1 g |
| Magnesium sulfate heptahydrate | 0.1 g |
| Thiamine hydrochloride | 20 mg |
| Sucrose | 100 g |
| Agar | 15 g |

4) Molecular-Biological Identification of the Strain Having the hycA Gene Disrupted The *Escherichia coli* W3110 strain having the hycA gene disrupted as obtained by the above-described procedure was identified with the strain having the hycA region deleted by the sequencer Prism 3100 Genetic Analyzer (produced by ABI Co.).

5) Preparation of the Vector for Highly Expressing the fhlA Gene

From the genomic DNA as obtained under 1) described above, the DNA encoding fhlA and its upstream promoter region were amplified with use of a thermal cycler, GeneAmp PCR System 9700 (produced by ABI CO.) and using the below-described primer.

```
                                      (SEQ ID NO: 9)
GGGGTACCTAAAATTCTAAATCTCCTATATGTTAG (SEQ ID NO: 10)
CGGGATCCTGCGTCATCTCATCGATGACAA
```

The amplified DNA and plasmid pMW118 (produced by Nippon Gene Co. of Japan) were restriction-enzyme treated with KpnI, BamHI, followed by ligation with DNA Ligation kit ver 2.1 (produced by Takara Shuzo Co. of Japan) to give the vector fhlA-pMW118.

6) Introduction of the Vector and Preparation of the Strain Having the hycA Gene Disrupted and Capable of Highly Expressing the fhlA Gene The vector fhlA-pMW118 as obtained under 2) described above was introduced into the strain having the hycA gene disrupted through the electroporation method, followed by cultivation in the medium of Table 2 to give colonies of the objective strain having the hycA gene disrupted and capable of highly expressing the fhlA gene.

7) Molecular-Biological Identification of the High Expression of the fhlA Gene

The strain having the hycA gene disrupted and capable of highly expressing the fhlA gene as obtained by the above-described procedure was evaluated for high expression of the fhlA gene by the real-time RT-PCR method. The real-time RT-PCR method was carried out by following the below-described procedure. In the first place, the strain capable of highly expressing the fhlA gene and the wild strain were cultivated in the LB medium as described in Table 1 being supplemented with 20 mM of glucose (furthermore 50 mg/L of ampicillin for the strain capable of highly expressing the fhlA gene) anaerobically for 10 hours, and the total RNA was extracted from the resultant microbial cells with use of RNeasy Mini Kit (produced by QIAGEN Co.). The total RNA, the below-described primer for fhlA,

```
Fwd:  AGATCGTTTCTGTCGTCACCG    (SEQ ID NO: 11)

Rev:  CCGGCATAACAACTCATAGTCG   (SEQ ID NO: 12)
``` and QuantiTect SYBR Green RT-PCR (produced by QIAGEN Co.) were used to prepare a solution mixture as described in Table 4, followed by reverse transcription with use of ABI Prism 7000 Sequence Detection System (produced by ABI Co.) at 50° C. for 30 min, and thermal denaturation at 95° C. for 15 min, and DNA was synthesized by the thermal cycle of 40 cycles under the conditions of 95° C. for 15 sec. →57° C. for 20 sec. →60° C. for 1 min. The difference in expression of fhlA was examined from the difference in CT value as calculated from the DNA amplification curve through detection of the fluorescence intensity at each cycle. As a result, it was confirmed that the strain having hycA disrupted and capable of highly expressing fhlA exhibits more than 5-fold fhlA expression amount that of the wild strain.

As described above, the *Escherichia coli* W3110 strain transformed in this Example was named *Escherichia coli* W3110 ΔhycA/fhlA-pMW118 and has been deposited at international Patent Organism Depositary, National institute of Advanced science and Technology of Japan (under Accession No: FERM BP-10443).

Examples 6 to 8

Process for Producing Hydrogen with Use of *Escherichia Coli* W3110 Strain The Strain Capable of Highly Expressing the fhlA Gene and Having the hycA Gene Destroyed As Obtained in Example 5

1) Cultivation Under Aerobic Conditions

*Escherichia coli* W3110 strain (the strain capable of highly expressing the fhlA gene and having the hycA gene disrupted) was subjected to shake culture in 10 mL (Example 6), 200 mL (Example 7) and 2000 mL (Example 8) of the culture liquid having the composition as shown in Table 1 being supplemented with 50 mg/L of ampicillin overnight at 37° C. under aerobic conditions.

2).Cultivation Under Anaerobic Conditions for Imparting the Hydrogen Generation Capability to the Microorganism Then, the microorganism, which was yielded by subjecting the culture broth as obtained by shake culture overnight under aerobic conditions to a centrifuge (5,000 rpm, for 15 min) and removing the resultant supernatant liquid, was cultivated in 200 mL of the culture liquid having the composition as shown in Table 4 at 37° C. for 24 hours (Example 6) or 12 hours (Examples 7 and 8) so as to produce the microorganism possessing the hydrogen generation capability. On this occasion, cultivation under anaerobic conditions was initiated while setting the microorganism concentration at 0.04% by mass (Example 6), 1% by mass (Example 7) and 10% by mass (Example 8) relative to the mass of wet microbial cell, respectively, whereby 5N sodium hydroxide was added timely to maintain the pH at 6.0.

3) Investigation on the Hydrogen Generation Capability

The microorganism as cultivated under the conditions as described above under 2) was separated by centrifugation, and suspended in 50 mL of the solution for generating hydrogen having the composition as shown in above Table 5 (about 0.2% by mass of the microorganism concentration, relative to the mass of wet microbial cell; hereinafter referred to as "microorganism-suspended solution for generating hydrogen").

The microorganism-suspended solution for generating hydrogen as prepared in the above was admixed with sodium formate to 100 mM of the concentration of sodium formate to thereby measure the hydrogen generation capability of the microorganism.

The method of measuring the hydrogen generation capability of the microorganism was carried out by collecting by the method of replacement over the water the gas evolved immediately after dropwise addition of sodium formate. The initial rate of hydrogen generation was determined on the basis of the volume of the gas evolved for 30 sec beginning with addition of sodium formate. Analysis of the evolved gas by gas chromatography (manufactured by Shimadzu Co. of Japan) revealed that the gas contained 50% by volume of hydrogen and the remaining volume of gas (carbon dioxide).

The results are shown in FIG. 1.

Comparative Examples 1 to 3

Process for Producing Hydrogen with Use of *Escherichia coli* W3110 Strain (ATCC 27325)

Aerobic and anaerobic cultivations of the wild *Escherichia coli* W3110 strain (ATCC 27325) were conducted by following the below-described conditions and procedures corresponding individually to those of Examples 2, 3, 4, 6, 7 and 8, followed by determination of the respective initial rates of hydrogen generation.

For Comparative Example 1; the conditions and procedures equivalent to those of Examples 2 and 6.
For Comparative Example 2; the conditions and procedures equivalent to those of Examples 3 and 7.
For Comparative Example 3; the conditions and procedures equivalent to those of Examples 4 and 8.

The results are also shown in FIG. 1.

Figure 2:
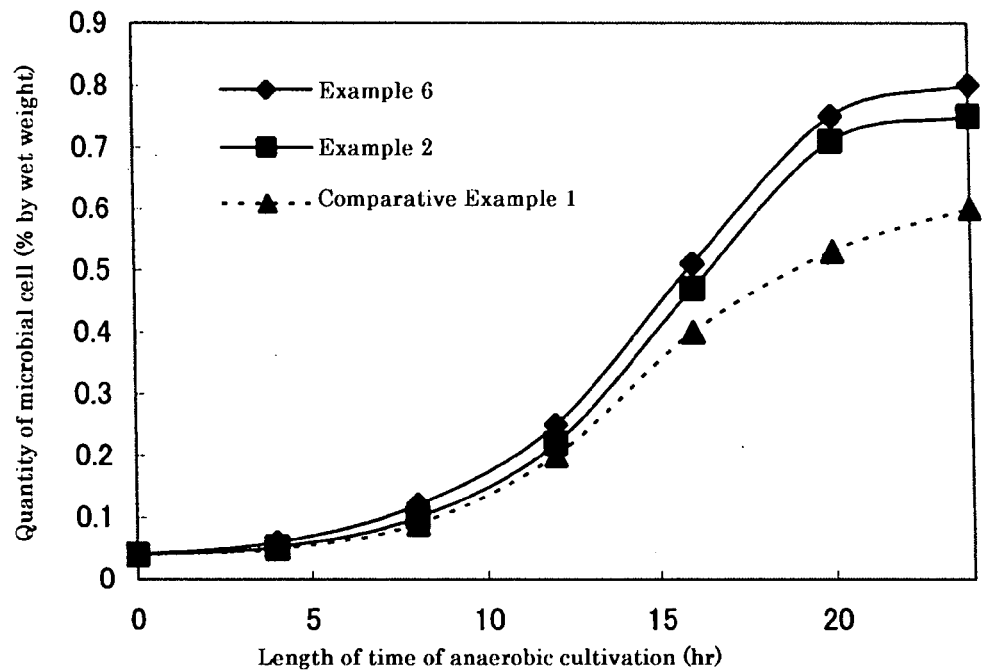
FIG. 2 is graphs showing the proliferation curves of Examples 2 and 6.

FIG. 2 shows the proliferation curves for the strains as obtained in Examples 2 and 6 and Comparative Example 1 when cultivated under anaerobic conditions.

It is clear and evident that the strains (obtained in Examples 2, 3 and 4) capable of highly expressing the fhlA gene according to the present invention exhibit outstandingly accelerated rate of hydrogen generation as compared with the wild strain. The strains as obtained in Examples 6, 7 and 8 are observed to produce the synergism of high expression of fhlA with destruction of hycA, and are found to exhibit by far improved hydrogen generation capability, as compared with the wild strain and the strain capable of highly expressing fhlA.

As demonstrated by FIG. 2, the recombinant microorganism of the present invention implies that it is feasible to acquire (cultivate) the microorganisms possessing more efficient, enhanced hydrogen generation capability, as compared with the wild strain.

Examples 9 to 11

Figure 5:
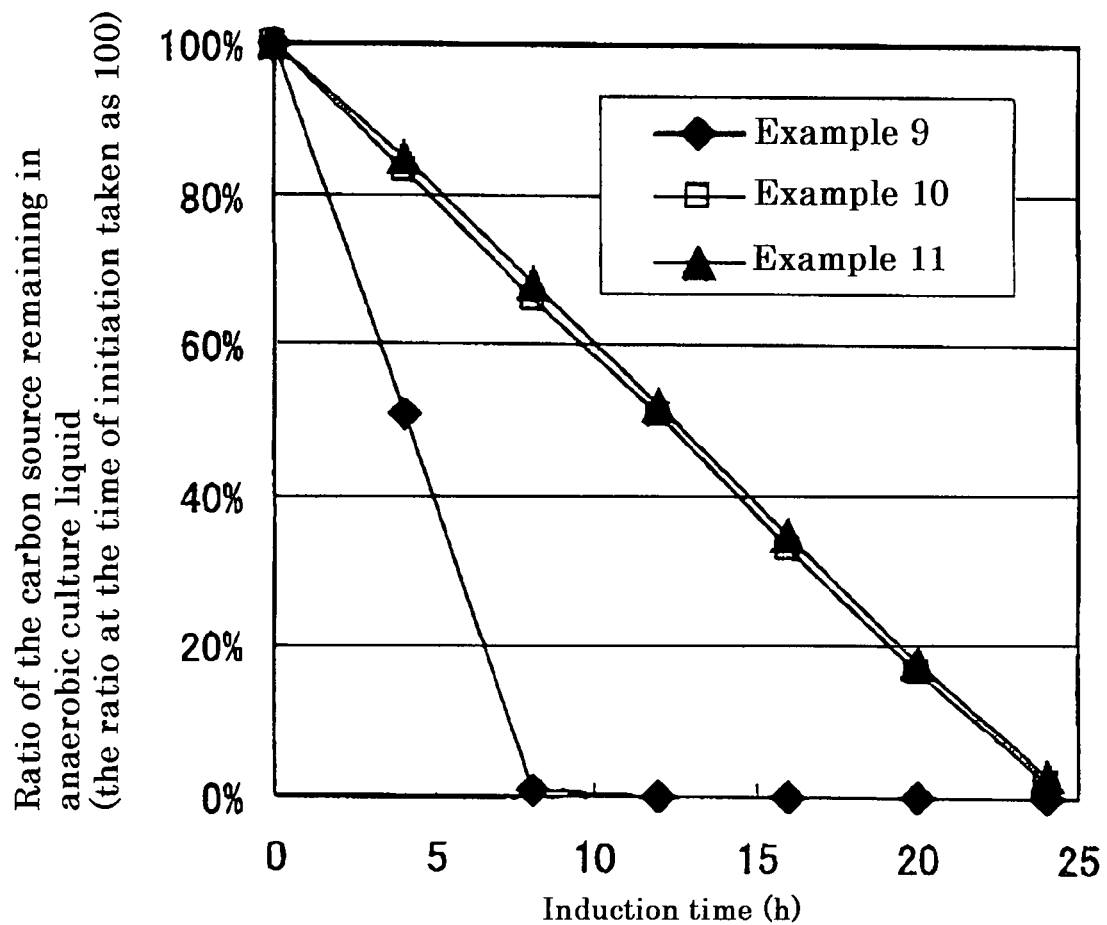
FIG. 5 is graphs showing time-course changes of the carbon source concentration in Examples 9, 10 and 11.
Figure 6:
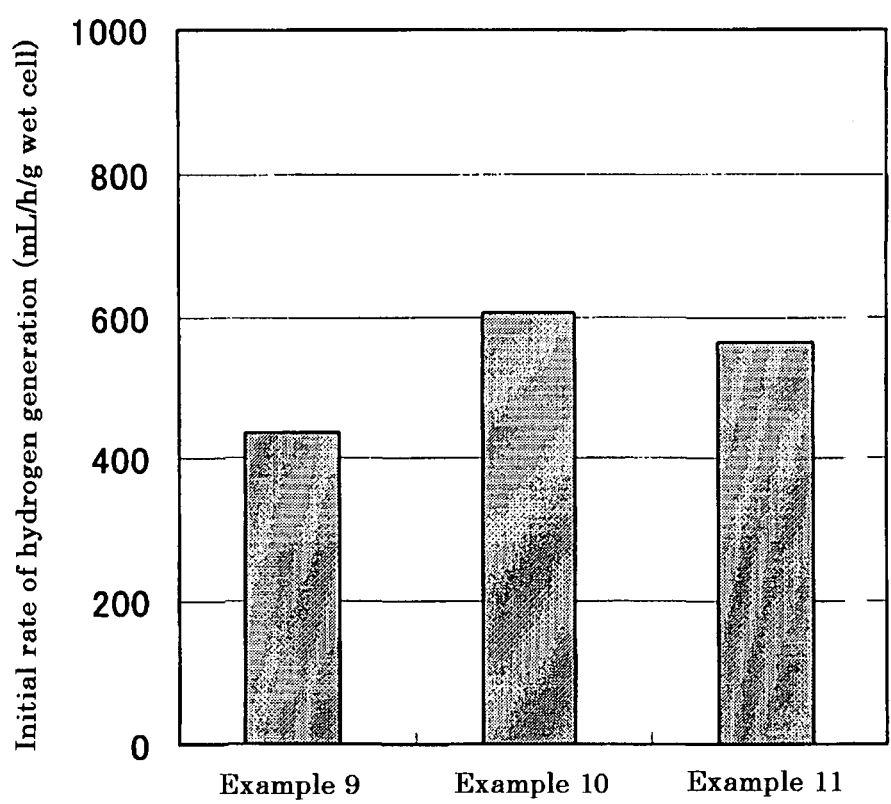
FIG. 6 is a graph showing the hydrogen-generation capabilities of the microorganisms of Examples 9, 10 and 11.

By following the procedure as described in Example 8 except that cultivation is carried out in the anaerobic culture liquid as shown in Table 8 for 24 hours, cultivation of *Escherichia coli* W3110 strain obtained in Example 5 (the strain capable of highly expressing the fhlA gene and having the hycA gene disrupted) under anaerobic conditions for imparting the hydrogen generation capability was conducted to investigate into the hydrogen generation capability. FIG. 5 shows time-course changes of the concentrations of the carbon sources (glucose, galactose and arabinose) used under anaerobic conditions as measured by high-pressure liquid chromatography. FIG. 6 shows the initial rates of hydrogen generation found when the carbon sources were used, respectively.

From FIG. 5, it was able to be confirmed that galactose and arabinose are the carbon sources with a slower metabolic rate than glucose, while FIG. 6 demonstrated that use of the carbon sources (galactose and arabinose) with a slower metabolic rate than glucose enables the microorganisms possessing the enhanced hydrogen generation capability to be acquired (cultivated).

TABLE 8

Composition of the anaerobic culture liquid

| Composition ingredient | Ingredient amount | | |
|---|---|---|---|
| | Example 9 | Example 10 | Example 11 |
| Water | 1000 mL | 1000 mL | 1000 mL |
| Glucose | 30 g | — | — |
| Galactose | — | 30 g | — |
| Arabinose | — | — | 30 g |
| Ammonium dihydrogenphosphate | 10 g | 10 g | 10 g |
| Potassium sulfate | 2 g | 2 g | 2 g |
| Sodium chloride | 0.3 g | 0.3 g | 0.3 g |
| Magnesium sulfate | 0.2 g | 0.2 g | 0.2 g |
| Iron sulfate | 4 mg | 4 mg | 4 mg |
| Zinc sulfate | 0.9 mg | 0.9 mg | 0.9 mg |
| Copper sulfate | 0.4 mg | 0.4 mg | 0.4 mg |
| Manganese sulfate | 0.2 mg | 0.2 mg | 0.2 mg |
| Calcium chloride | 0.8 mg | 0.8 mg | 0.8 mg |
| Sodium tetraborate | 0.09 mg | 0.09 mg | 0.09 mg |
| Ammonium heptamolybdate (-6) | 0.4 mg | 0.4 mg | 0.4 mg |
| Ammonium nickel sulfate | 0.9 mg | 0.9 mg | 0.9 mg |
| Sodium selenite | 0.6 mg | 0.6 mg | 0.6 mg |
| Ampicillin Sodium | 50 mg | 50 mg | 50 mg |

Industrial Applicability

Utilization of the microorganism of the present invention enables the hydrogen production from an organic substrate to be accomplished on a practical, commercial scale. The hydrogen to be produced by this invention, which is free of carbon monoxide being causative to poisoning of the electrode catalyst for fuel cells, is useful as a fuel for fuel cells.

The invention claimed is:

1. A transformant of *Escherichia coli* comprising an endogenous formate dehydrogenase gene, an endogenous hydrogenase gene, and an exogenous transcription activator gene for formate hydrogen lyase (FHL) system, said transcription activator being highly expressed in said transformant, said transformant further comprising an inactivated endogenous hycA gene, wherein said exogenous transcription activator gene is a fhlA gene from *Escherichia coli*.

2. The transformant of *Escherichia coli* according to claim 1, wherein *Escherichia coli* is *Escherichia coli* W3110 strain (ATCC 27325).

3. *Escherichia coli* W3110/fhlA-pMW118 strain (Deposited at International Patent Organism Depository Center, National Institute of Advanced Industrial Science and Technology, under Accession No. FERM BP-10444).

4. *Escherichia coli* W3110 ΔhycA/fhlA-pMW118 strain (Deposited at International Patent Organism Depository Center, National Institute of Advanced Industrial Science and Technology, under Accession No. FERM BP-10443).

5. A process for producing hydrogen, wherein said process comprises cultivating a microorganism according to claim 1 under aerobic conditions, followed by further cultivation under anaerobic conditions, and cultivating the said cultivated microorganism in a solution for hydrogen generation under feeding of an organic substrate.

6. A process for producing hydrogen according to claim 5, wherein said further cultivation comprises admixture of a carbon source with a slower metabolic rate than glucose.

7. A process for producing hydrogen according to claim 6, wherein the carbon source with a slower metabolic rate than glucose is galactose or arabinose.

8. The microorganism of claim 1 wherein the fhlA gene is an *Escherichia coli* K-12 W3110 strain fhlA gene.

9. The microorganism of claim 1 wherein the hycA gene is an *Escherichia coli* K-12 W3110 strain hycA gene.

10. A transformant of *Escherichia coli* K-12 W3110 strain (ATCC 27325) comprising an endogenous formate dehydrogenase gene, an endogenous hydrogenase gene, and an exogenous transcription activator gene for formate hydrogen lyase (FHL) system, said transcription activator being highly expressed in said transformant, said transformant further comprising an inactivated endogenous hycA gene, wherein said exogenous transcription activator gene is a fhlA gene from *Escherichia coli*.

11. A transformant of *Escherichia coli* K-12 W3110 strain (ATCC 27325) comprising an endogenous formate dehydrogenase gene, an endogenous hydrogenase gene, and an exogenous transcription activator gene for formate hydrogen lyase (FHL) system, said transcription activator being highly expressed in said transformant, said transformant further comprising an inactivated endogenous hycA gene, wherein said exogenous transcription activator activator gene is a fhlA gene from *Escherichia coli* K-12 W3110 strain.

* * * * *

SEQUENCE LISTING

<160> NUMBER OF SEQ ID NOS: 14

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggggtaccta aaattctaaa tctcctatat gttag                              35

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgggatcctg cgtcatctca tcgatgacaa                                    30

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agatcgtttc tgtcgtcacc g                                             21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccggcataac aactcatagt cg                                            22

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctctggatcc atttcatctt cgggcgtgc                                     29

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctctgagctc aaaggtcaca tttgacggcg                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctctgcatgc aacccatcac atatacctgc                                    30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctctgcatgc atcgatcctc tagagtatcg                                    30

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggggtaccta aaattctaaa tctcctatat gttag                              35

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgggatcctg cgtcatctca tcgatgacaa                                    30

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agatcgtttc tgtcgtcacc g                                             21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccggcataac aactcatagt cg                                            22

<210> SEQ ID NO 13
<211> LENGTH: 2079
<212> TYPE: DNA
<213> ORGANISM: Escherichia coli

<400> SEQUENCE: 13

| | | | | | |
|---|---|---|---|---|---|
| atgtcatata | caccgatgag | tgatctcgga | caacaagggt | tgttcgacat | cactcggaca | 60 |
| ctattgcagc | agcccgatct | ggcctcgctg | tgtgaggctc | tttcgcaact | ggtaaagcgt | 120 |
| tctgcgctcg | ccgacaacgc | ggctattgtg | ttgtggcaag | cgcagactca | acgtgcgtct | 180 |
| tattacgcgt | cgccgtgaaaa | agacacccccc | attaaatatg | aagacgaaac | tgttctggca | 240 |
| cacggtccgg | tacgcagcat | tttgtcgcgc | cctgatacgc | tgcattgcag | ttacgaagaa | 300 |
| tttgtgaaa | cctggccgca | gctggacgca | ggtgggctat | acccaaaatt | tggtcactat | 360 |
| tgcctgatgc | cactggcggc | ggaagggcat | atttttggtg | gctgtgaatt | tattcgttat | 420 |
| gacgatcgcc | cctggagcga | aaaagagttc | aatcgtctgc | aaacatttac | gcagatcgtt | 480 |
| tctgtcgtca | ccgaacaaat | ccagagccgc | gtcgttaaca | atgtcgacta | tgagttgtta | 540 |
| tgccgggaac | gcgataactt | ccgcatcctg | gtcgccatca | ccaacgcggt | gctttcccgc | 600 |
| ctggatatgg | acgaactggt | cagcgaagtc | gccaaagaaa | tccattacta | tttcgacatt | 660 |
| gacgatatca | gtatcgtctt | acgcagccac | cgtaaaaaca | aactcaacat | ctactccact | 720 |
| cactatcttg | ataaacagca | tcccgcccac | gaacagagcg | aagtcgatga | agccggaacc | 780 |
| ctcaccgaac | gcgtgttcaa | aagtaaagag | atgctgctga | tcaatctcca | cgagcgggac | 840 |
| gatttagccc | cctatgaacg | catgttgttc | gacacctggg | gcaaccagat | tcaaaccttg | 900 |
| tgcctgttac | cgctgatgtc | tggcgacacc | atgctgggcg | tgctgaaact | ggcgcaatgc | 960 |
| gaagagaaag | tgtttaccac | taccaatctg | aatttactgc | gccagattgc | cgaacgtgtg | 1020 |
| gcaatcgctg | tcgataacgc | cctcgcctat | caggaaatcc | atcgtctgaa | agaacggctg | 1080 |
| gttgatgaaa | acctcgccct | gaccgagcag | ctcaacaatg | ttgatagtga | atttggcgag | 1140 |
| attattggcc | gcagcgaagc | catgtacagc | gtgcttaaac | aagttgaaat | ggtggcgcaa | 1200 |
| agtgacagta | ccgtgctgat | cctcggtgaa | actggcacgg | gtaaagagct | gattgcccgt | 1260 |
| gcgatccata | atctcagtgg | gcgtaataat | cgccgcatgg | tcaaaatgaa | ctgcgcggcg | 1320 |
| atgcctgccg | gattgctgga | aagcgatctg | tttggtcatg | agcgtggggc | ttttaccggt | 1380 |
| gccagcgccc | agcgtatcgg | tcgttttgaa | ctggcggata | aagctcccct | gttcctcgac | 1440 |
| gaagtgggcg | atatgccact | ggagttacag | ccgaagttgc | tgcgtgtatt | gcaggaacag | 1500 |
| gagtttgaac | gtctcggcag | caacaaaatc | attcagacgg | acgtgcgtct | aatcgccgcg | 1560 |
| actaaccgcg | atctgaaaaa | aatggtcgcc | gaccgtgagt | tccgtagcga | tctctattac | 1620 |
| cgcctgaacg | tattcccgat | tcacctgccg | ccactacgcg | agcgtccgga | agatattccg | 1680 |
| ctgctggcga | aagcctttac | cttcaaaatt | gcccgtcgtc | tggggcgcaa | tatcgacagc | 1740 |
| attcctgccg | agacgctgcg | caccttgagc | aacatggagt | ggccgggtaa | cgtacgcgaa | 1800 |
| ctggaaaacg | tcattgagcg | cgcggtattg | ctaacacgcg | gtaacgtgct | gcagctgtca | 1860 |
| ttgccagata | ttgtttttacc | ggaacctgaa | acgccgcctg | ccgcaacggt | tgtcgccctg | 1920 |
| gagggcgaag | atgaatatca | gttgattgtg | cgcgtgctga | agaaaccaa | cggcgtggtt | 1980 |
| gccgggccta | aaggcgctgc | gcaacgtctg | gggctgaaac | gcacgaccct | gctgtcacgg | 2040 |
| atgaagcggc | tgggaattga | taaatcggca | ttgatttaa | | | 2079 |

<210> SEQ ID NO 14

```
<211> LENGTH: 462
<212> TYPE: DNA
<213> ORGANISM: Escherichia coli

<400> SEQUENCE: 14
atgactattt gggaaataag cgagaaagcc gattacatcg cacagcggca tcgtcgccta        60
caggaccagt ggcacatcta ctgcaattcg ctggttcagg ggatcacgtt atcgaaagcg       120
cgcctgcatc acgccatgag ctgcgcgccg gacaaagaac tctgtttcgt ccttttttgaa      180 cattttcgca tttacgtcac cctggcggat ggctttaaca gccacaccat cgagtattac       240
gtcgaaacaa aagatggcga agacaaacag cggattgcgc aggcgcaact gagcattgac       300
ggcatgattg atggcaaggt caacatccgc gatcgcgaac aggttctgga acactatctc       360
gaaaaaatcg ctggcgttta cgacagctta tacaccgcta ttgaaaacaa tgtgccggtg       420
aatttaagcc aactggtaaa gggacaaagc ccggcagcat ga                         462
```